(12) United States Patent
Lenagh et al.

(10) Patent No.: US 10,571,419 B2
(45) Date of Patent: Feb. 25, 2020

(54) CONTACTING TYPE FLOW THROUGH CONDUCTIVITY CELL

(71) Applicant: Rosemount Aerospace Inc., Burnsville, MN (US)

(72) Inventors: Thomas Lenagh, Farmington, MN (US); Rudy Pitera, Woodbury, MN (US); Tomas Lorincz, Savage, MN (US)

(73) Assignee: Rosemount Aerospace Inc., Burnsville, MN (US)

( * ) Notice: Subject to any disclaimer, the term of this patent is extended or adjusted under 35 U.S.C. 154(b) by 305 days.

(21) Appl. No.: 15/604,231

(22) Filed: May 24, 2017

(65) Prior Publication Data
US 2018/0340905 A1    Nov. 29, 2018

(51) Int. Cl.
*G01N 27/08*    (2006.01)
*G01N 27/07*    (2006.01)

(52) U.S. Cl.
CPC .............. *G01N 27/08* (2013.01); *G01N 27/07* (2013.01)

(58) Field of Classification Search
CPC ...... G01N 17/00; G01N 17/002; G01N 17/02; G01N 17/006; G01N 27/06; G01N 27/07; G01N 27/08
USPC .................................................. 324/701, 693
See application file for complete search history.

(56) References Cited

U.S. PATENT DOCUMENTS

| | | | |
|---|---|---|---|
| 3,082,372 A * | 3/1963 | Gauthier | G01N 27/07 324/446 |
| 3,617,868 A * | 11/1971 | Beitel | E21B 49/005 324/376 |
| 4,118,663 A | 10/1978 | Barben, II | |
| 4,724,394 A | 2/1988 | Langer et al. | |
| 5,441,049 A * | 8/1995 | Masano | G01N 27/07 324/446 |
| 5,708,363 A | 1/1998 | Yates et al. | |
| 5,729,005 A * | 3/1998 | MacDougall | G01R 15/246 250/227.17 |
| 5,770,795 A * | 6/1998 | Behar | G01N 11/14 73/54.23 |
| 6,122,956 A * | 9/2000 | Klausner | G01N 27/08 324/439 |
| 6,369,579 B1 | 4/2002 | Riegel | |
| 7,078,909 B2 | 7/2006 | Feng et al. | |
| 7,183,778 B2 * | 2/2007 | Homan | G01V 3/20 324/693 |
| 7,772,854 B2 | 8/2010 | Rezvani | |
| 8,264,241 B2 | 9/2012 | Slezak et al. | |
| 8,521,442 B2 | 8/2013 | Wang | |

(Continued)

*Primary Examiner* — Patrick Assouad
*Assistant Examiner* — Robert P Alejnikov, Jr.
(74) *Attorney, Agent, or Firm* — Kinney & Lange, P.A.

(57) ABSTRACT

A conductivity cell includes a cylindrical flow tube holder having a closed first end and an open second end, a first end fitting positioned on the first end of the flow tube holder, a second end fitting positioned on the second end of the flow tube holder, a flow tube positioned within the flow tube holder, an end cap positioned in the open second end of the flow tube holder and adjacent the flow tube and the second end fitting, a plurality of electrodes positioned in the flow tube, a plurality of o-rings positioned on the electrodes, and a flow through hole extending from the first end fitting through the flow tube holder, the flow tube, and the end cap to the second end fitting. The plurality of electrodes are press-fit into the flow tube.

21 Claims, 8 Drawing Sheets

(56) References Cited

U.S. PATENT DOCUMENTS

| | | |
|---|---|---|
| 8,525,534 B2 | 9/2013 | Brandt et al. |
| 9,035,661 B2 | 5/2015 | Andersson et al. |
| 9,488,611 B2 | 11/2016 | Rezvani et al. |
| 10,197,546 B2 | 2/2019 | Rahaliou et al. |
| 2005/0013595 A1 | 1/2005 | Israelson et al. |
| 2009/0007642 A1 | 1/2009 | Busby et al. |
| 2012/0256641 A1* | 10/2012 | Andersson ............. G01N 27/07 324/649 |
| 2013/0036817 A1 | 2/2013 | Lucas et al. |
| 2013/0144548 A1 | 6/2013 | Xie |

* cited by examiner

CONTACTING TYPE FLOW THROUGH CONDUCTIVITY CELL

STATEMENT OF GOVERNMENT INTEREST

This invention was made with government support under NNH16C087C awarded by NASA. The government has certain rights in the invention.

BACKGROUND

The present disclosure relates generally to sensors, and in particular, to sensors for measuring liquid conductivity.

Liquid conductivity measurement is used to determine the ionic make up of a solution. A conductivity cell can measure liquid conductivity using electrodes that generate a current in the solution and measure the resulting voltage. A conductivity cell with improved sealing and increased stability and accuracy of measurement is needed.

SUMMARY

A conductivity cell includes a cylindrical flow tube holder having a closed first end and an open second end, a first end fitting positioned on the first end of the flow tube holder, a second end fitting positioned on the second end of the flow tube holder, a flow tube positioned within the flow tube holder, an end cap positioned in the open second end of the flow tube holder and adjacent the flow tube and the second end fitting, a plurality of electrodes positioned in the flow tube, a plurality of o-rings positioned on the electrodes, and a flow through hole extending from the first end fitting through the flow tube holder, the flow tube, and the end cap to the second end fitting. The plurality of electrodes are press-fit into the flow tube.

A conductivity cell includes a cylindrical flow tube holder having a closed first end and an open second end, a first end fitting positioned on the first end of the flow tube holder, a second end fitting positioned on the second end of the flow tube holder, a flow tube positioned within the flow tube holder, an end cap positioned in the open second end of the flow tube holder and adjacent the flow tube and the second end fitting, a plurality of electrodes positioned in the flow tube, and a flow through hole extending from the first end fitting through the flow tube holder, the flow tube, and the end cap to the second end fitting. Each electrode includes a main body, a stem extending from an inner end of a main body, a groove on the inner end of the main body of the electrode, the groove surrounding the stem, and a groove extending around a side of the main body, the side located between the inner end of the main body and an outer end of main body. An o-ring is positioned in each of the grooves on the electrodes. The plurality of electrodes are press-fit into the flow tube.

A conductivity cell includes a cylindrical flow tube holder having a closed first end and an open second end, a first end fitting positioned on the first end of the flow tube holder, a second end fitting positioned on the second end of the flow tube holder, a flow tube positioned within the flow tube holder, an end cap positioned in the open second end of the flow tube holder and adjacent the flow tube and the second end fitting, a plurality of electrodes positioned in the flow tube, a plurality of o-rings positioned on the electrodes, and a flow through hole extending from the first end fitting through the flow tube holder, the flow tube, and the end cap to the second end fitting. The flow tube is press fit into the flow tube holder.

DETAILED DESCRIPTION

In general, the present disclosure describes a contacting type flow through conductivity cell for measuring liquid conductivity. The conductivity cell has electrodes with o-rings, the electrodes being press-fit into a flow tube, which is press-fit into a flow tube holder, to yield proper squeeze and engagement of the o-rings. As a result, the o-rings form seals to ensure that the liquid in a flow through hole of the conductivity cell does not leak into the internal components of the cell. Additionally, in one embodiment, four electrodes are on each side of the flow tube such that there are four sets of electrodes, two sets of current electrodes and two sets of voltage electrodes, with each set including two opposing electrodes connected in parallel for a more uniform voltage and more stable and sensitive conductivity measurement. The circuitry of the cell includes a Wheatstone bridge connected to the current electrodes and an instrumentation amplifier connected to the voltage electrodes that are positioned between the current electrodes, which results in high accuracy of the conductivity measurement near the target conductivity point.

Figure 1A:
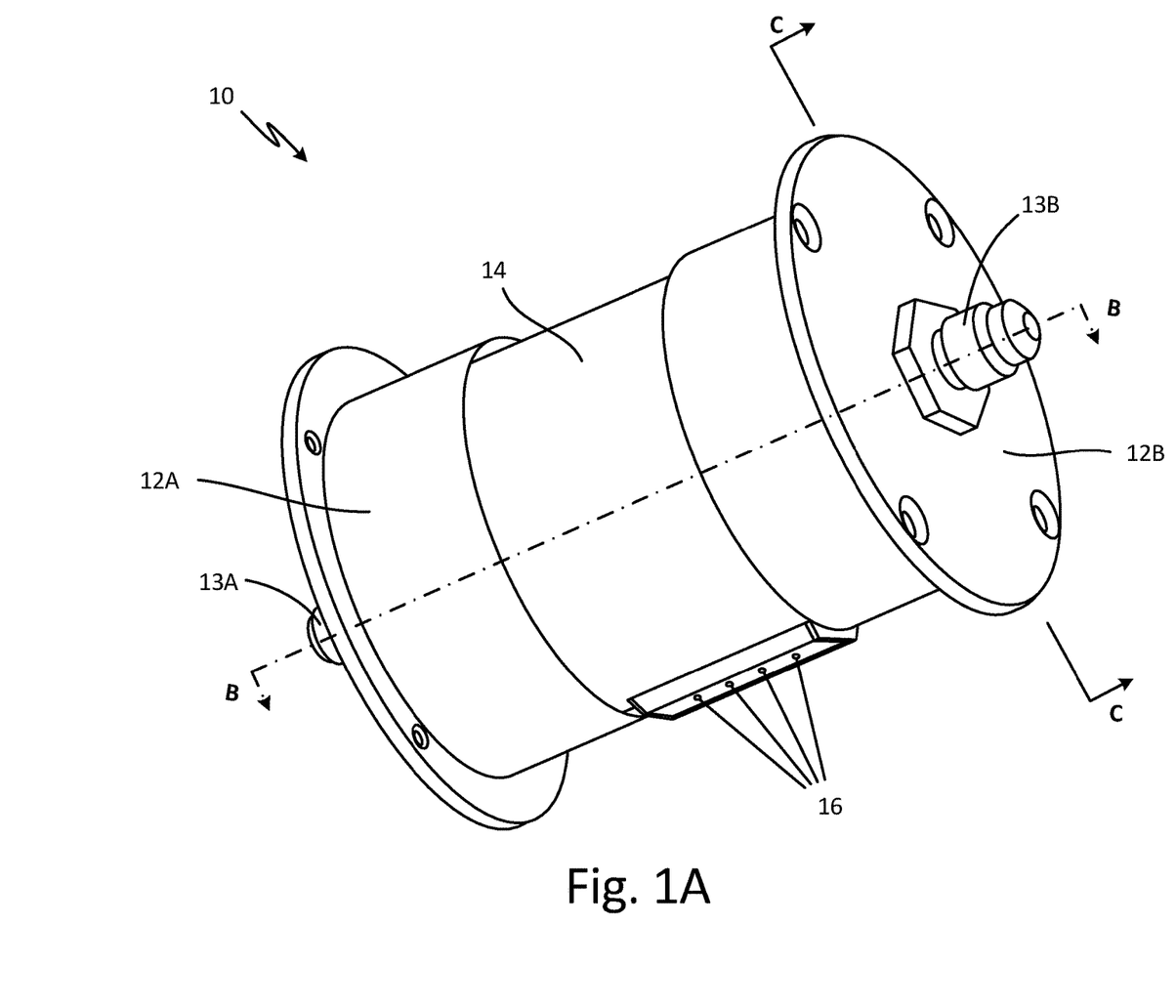
FIG. 1A is an isometric view of a conductivity cell.

FIG. 1A is an isometric view of conductivity cell 10. Conductivity cell 10 includes first end fitting 12A with inlet nipple 13A and second end fitting 12B with outlet nipple 13B, flow tube holder 14, and electrical wiring holes 16.

End fittings 12A, 12B are positioned on cylindrical flow tube holder 14. First end fitting 12A has inlet nipple 13A and is positioned on a first end of flow tube holder 14, and second end fitting 12B has outlet nipple 13B and is positioned on a second end of flow tube holder 14. End fittings 12A, 12B are connected via inlet nipple 13A and outlet nipple 13B to a fluid line (not shown) containing a fluid to be measured. End fittings 12A, 12B are made of stainless steel. Flow tube holder 14 is made of plastic. Electrical wiring holes 16 are passageways extending from an interior of flow tube holder 14 to an exterior of flow tube holder 14. Conductivity cell 10 has four electrical wiring holes 16.

End fittings 12A, 12B connect conductivity cell 10 to a fluid line (not shown) such that conductivity cell 10 in installed in-line with the fluid. Conductivity cell 10 is also connected to circuitry via wires, which exit flow tube holder 14 of conductivity cell 10 through electrical wiring holes 16. Conductivity cell 10 measures the conductivity of the fluid in the fluid line. The conductivity measurement indicates the ionic make-up of the fluid or how dirty the fluid is.

Figure 1B:
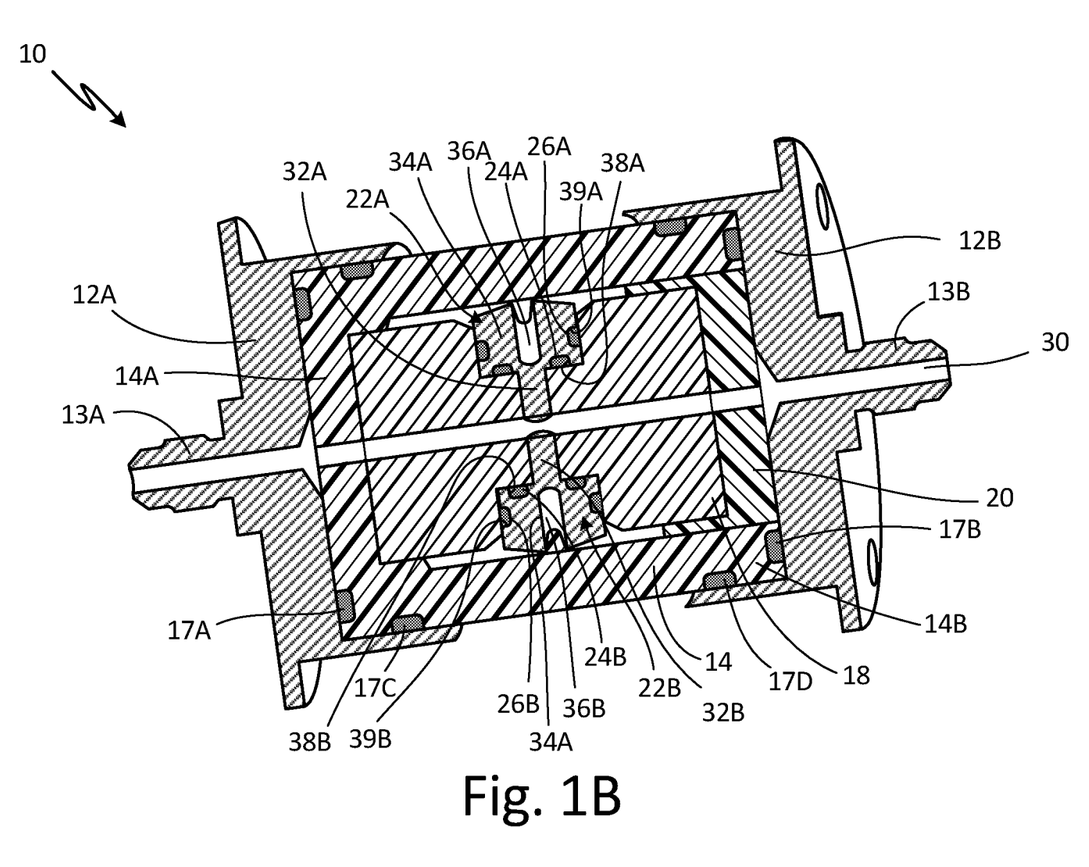
FIG. 1B is an isometric cross-sectional view of the conductivity cell taken along line B-B of FIG. 1A.
Figure 1C:
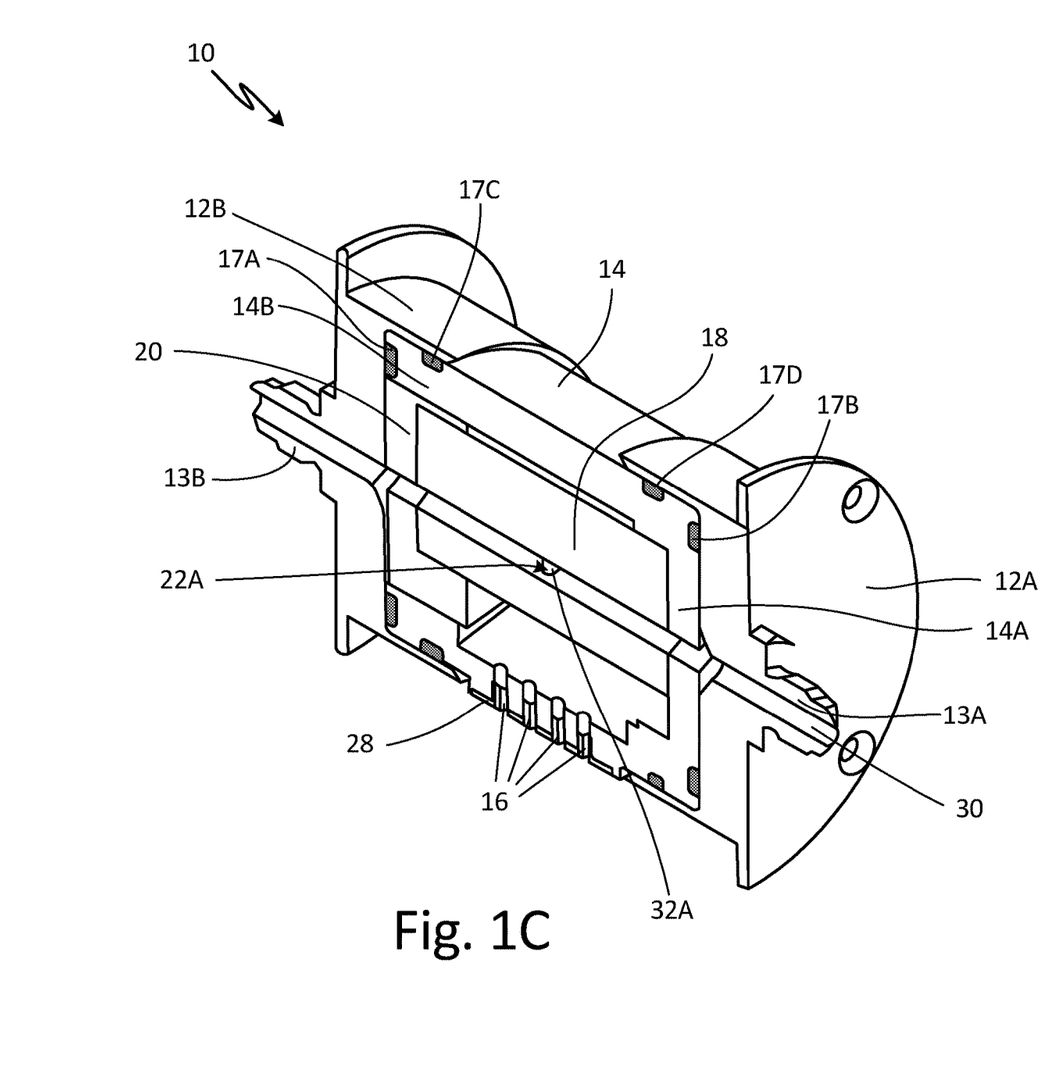
FIG. 1C is an isometric cross-sectional view of the conductivity cell taken along line C-C of FIG. 1A.

FIG. 1B is an isometric cross-sectional view of conductivity cell 10 taken along line B-B of FIG. 1A. FIG. 1C is an isometric cross-sectional view of conductivity cell 10 taken along line C-C of FIG. 1A. FIGS. 1B and 1C will be discussed together. In addition to the elements shown in FIG. 1A, conductivity cell 10 includes end fittings 12A, 12B, flow tube holder 14 having first end 14A and second end 14B, o-rings 17A, 17B, 17C, and 17D, flow tube 18, end cap 20, electrode pair 22A, 22B (shown in FIG. 1B), face o-rings 24A and 24B (shown in FIG. 1B), rod o-rings 26A and 26B (shown in FIG. 1B), epoxy 28 (shown in FIG. 1C), and flow-through hole 30. Electrodes 22A and 22B include stems 32A and 32B, main bodies 34A and 34B (shown in FIG. 1B), holes 36A and 36B (shown in FIG. 1B), grooves 38A and 38B (shown in FIG. 1B), and grooves 39A and 39B (shown in FIG. 1B), respectively.

Flow tube holder 14 has first end 14A that is closed and second end 14B that is open. O-ring 17A is a face o-ring positioned at first end 14A of flow tube holder 14 and adjacent first end fitting 12A. O-ring 17B is a face o-ring positioned at second end 14B of flow tube holder 14 and adjacent second end fitting 12B. O-ring 17C is a circumferential o-ring positioned around first end 14A of flow tube holder 14 and adjacent first end fitting 12A. O-ring 17D is a circumferential o-ring positioned around second end 14B of flow tube holder 14 and adjacent second end fitting 12B. Flow tube 18 is press-fit into flow tube holder 14 through open second end 14B of flow tube holder 14 such that flow tube holder 14 surrounds flow tube 18. Flow tube 18 is made of plastic. Mating faces of flow tube holder 14 and flow tube 18 are glued together with epoxy. End cap 20 is press-fit into open second end 14B of flow tube holder 14 such that it is positioned adjacent flow tube 18 and second end fitting 12B. End cap 20 is positioned to seal off open second end 14B of flow tube holder 14. End cap 20 is glued to flow tube holder 14. End cap 20 is made of plastic.

Electrode pair 22A, 22B is seated in flow tube 18. More specifically, electrodes 22A and 22B are press-fit into flow tube 18 before flow tube 18 is press-fit into flow tube holder 14. Flow tube holder 14 has an inner diameter sized to ensure electrodes 22A and 22B remain properly pressed into flow tube 18, outer ends of electrodes 22A and 22B being in contact with an inner wall of flow tube holder 14. Flow tube 14 press-fits electrodes 22A and 22B to control the axial and radial positions of electrodes 22A and 22B. Electrodes 22A and 22B are made of nickel alloy. Conductivity cell 10 has one electrode pair 22, with one electrode 22A in a first side of flow tube 18 and one electrode 22B in a second side of flow tube 18. Face o-rings 24A and 24B and rod o-rings 26A and 26B are positioned on each of electrodes 22A and 22B, respectively. Face o-rings 24A and 24B and rod o-rings 26A and 26B contact electrodes 22A and 22B, respectively, and flow tube 18. A first end of a first wire (not shown), is connected via brazing to electrode 22A and a first end of a second wire (not shown), is connected via brazing to electrode 22B. Wires exit flow tube holder 14 through electrical wiring holes 16 such that second ends of wires are located outside flow tube holder 14. O-rings (not shown) are positioned around wires in electrical wiring holes 16, two o-rings being positioned in each electrical wiring hole 16. Epoxy 28 is positioned in electrical wiring holes 16 adjacent the wires and the o-rings. Epoxy 28 fills in each electrical wiring hole 16 such that epoxy 28 is flush with an exterior surface of flow tube holder 14.

Flow-through hole 30 extends through conductivity cell 10 from first end fitting 12A to second end fitting 12B. Flow-through hole 30 is formed by inner diameters of first end fitting 12A, a first end 14B of flow tube holder 14, flow tube 18, electrodes 22A and 22B, end cap 20, and second end fitting 12B.

Each of electrodes 22A and 22B has a similar structure. The components of electrodes 22A and 22B are the same and will be described with reference to electrode 22A. Electrode 22A has cylindrical stem 32A extending from an inner end of main body 34A to flow-through hole 30. Stem 32A extends through flow tube 18 such that an inner end of stem 32A is flush with the inner diameter of flow tube 18. Stem 32A is positioned to be in contact with fluid in flow-through hole 30. Electrode 22A has hole 36A extending into a center of main body 34A from an outer end of main body 34A. Hole 36A holds a thermistor (not shown) in electrode 22A. A wire (not shown) connects the thermistor in electrode 22A to circuitry 40 (shown in FIG. 2). In alternate embodiments, electrode 22A does not include hole 36A. Main body 34A of electrode 22A has annular grooves 38A and 39A. Groove 38A is located in the inner end of main body 34A, and groove 39A is located around main body 34A between the inner end of main body 34A and the outer end of main body 34A. Groove 38A is configured to receive face o-ring 24A and groove 39A is configured to receive rod o-ring 26A. As such, face o-ring 24A is positioned around stem 32A of electrode 22A, and rod o-ring 26A is positioned around main body 34A of electrode 22A. In alternate embodiments, electrodes 22A and 22B can be sized and shaped to correspond to the desired operating point of conductivity.

Flow tube holder 14, flow tube 18, and end cap 20 have initial inner diameters smaller than the desired diameter of flow-through hole 30. Stems 32A and 32B of electrodes 22A and 22B are initially longer than desired such that stems 32A and 32B protrude into flow-through hole 30. After the conductivity cell 10 has been assembled, epoxied together, and cured, flow-through hole 30 is reamed out to yield a final desired diameter of flow-through hole 30. After flow-through hole 30 has been reamed out, ends of stems 32A and 32B making up flow-through hole 30 are curved and concave as they are flush with the inner diameter of flow tube 18. End fittings 12A and 12B have inner diameters equal to the desired diameter of flow-through hole 30 and do not get reamed out.

Ending fittings 12 connect conductivity cell 10 to a fluid line (not shown) such that conductivity cell 10 is installed in-line with the fluid. Fluid from the fluid line runs through conductivity cell 10 through flow-through hole 30. O-rings 17A and 17C provide sealing between first end 14A of flow tube holder 14 and first end fitting 12A. O-rings 17B and 17D provide sealing between second end 14B of flow tube holder 14 and second end fitting 12. Face o-rings 24A and 24B and rod o-rings 26A and 26B provide sealing between flow tube 18 and electrodes 22A and 22B. Flow tube holder 14, flow tube 18, and end cap 20 are plastic so that electrodes 22A and 22B are the only metal in contact with fluid in flow-through hole 30 in flow tube holder 14. Fluid in flow-through hole 30 is energized by electrode pair 22A, 22B, and the resistance of the fluid between electrodes 22A and 22B is measured by electrode pair 22A, 22B. The wires connected to electrodes 22A and 22B connect electrode pair 22A, 22B to external circuitry required for electrodes 22A and 22B to energize the fluid and measure the resistance of the fluid. The wires exit flow tube holder 14 through electrical wiring holes 16 and open centers of the two o-rings in electrical wiring holes 16, which center the wires as they exit electrical wiring holes 16 to reach the external circuitry. Epoxy 28 fills in electrical wiring holes 16 to secure and support the wires as they exit flow tube holder 14, to seal flow tube holder 14 from leakage, and to secure flow tube 18 from creeping, rotating, or moving.

Reaming to create flow-through hole 30 ensures electrodes 22A and 22B are properly distanced with a high degree of precision. Reaming also ensures flow tube 18, flow tube holder 14, and end cap 20 all have the same inner diameters and ensures that flow-through hole 30 is smooth and continuous. As a result, flow-through hole 30 does not include edges where a bubble from fluid in flow-through hole 30 could collect. Electrodes 22A and 22B are press-fit into flow tube 18 and flow tube 18 is press-fit into flow tube holder 14 to yield proper squeeze and engagement of face o-rings 24A and 24B on stems 32A and 32B of electrodes 22A and 22B, respectively, and proper axial and radial positioning of electrodes 22A and 22B. Face o-rings 24A and 24B and rod o-rings 26A and 26B provide water-tight sealing between flow tube 18 and electrodes 22A and 22B to ensure the fluid in flow-through hole 30 does not leak past electrodes 22A and 22B, respectively, and into other internal components of conductivity cell 10. The design of conductivity cell 10 also makes it easy to manufacture.

Figure 2:
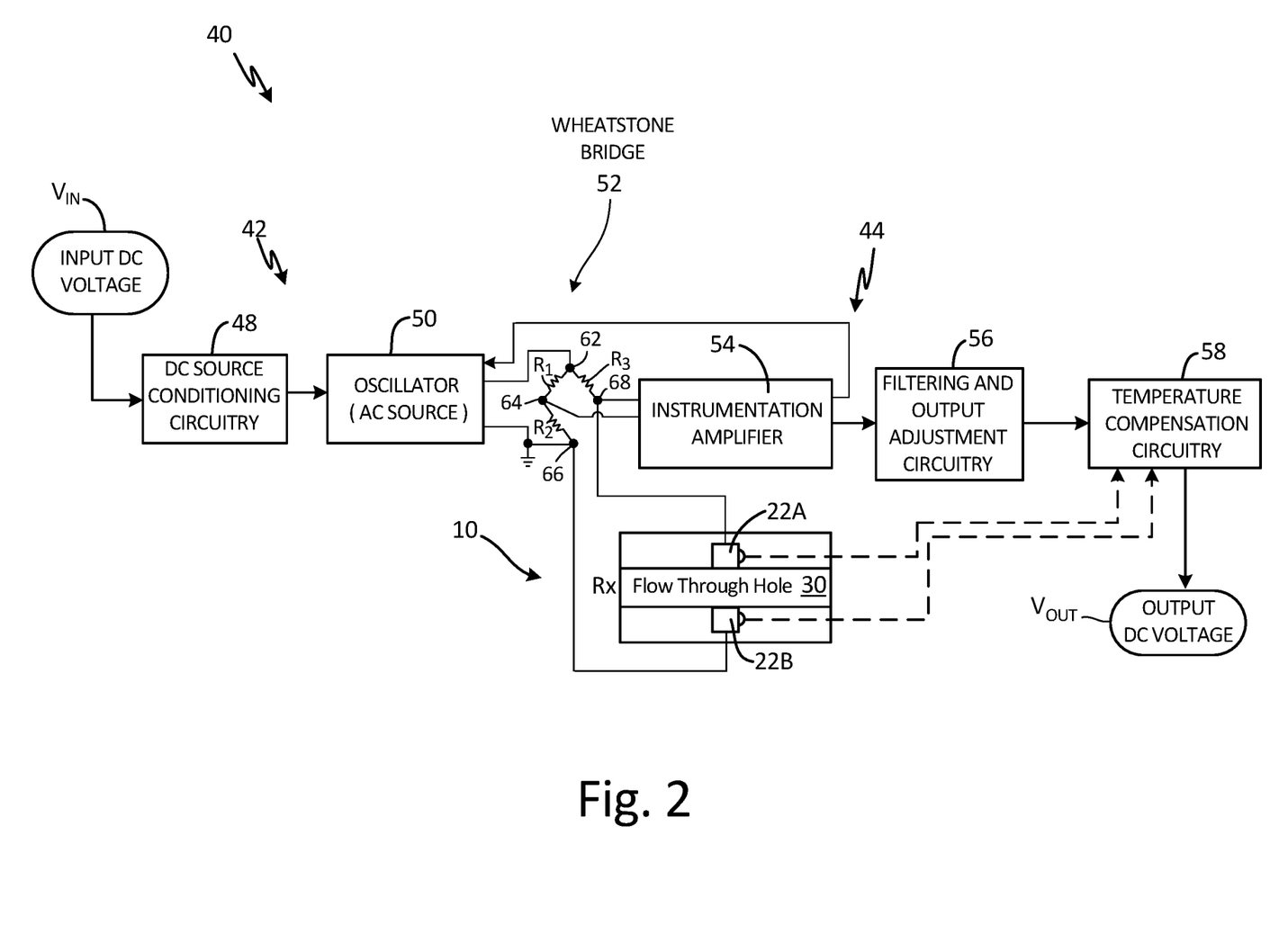
FIG. 2 is a block diagram showing circuitry connected to the conductivity cell.

FIG. 2 is a block diagram showing circuitry 40 connected to conductivity cell 10. Conductivity cell 10 includes electrode pair 22A, 22B and flow-through hole 30. Circuitry 40 includes sensor drive circuitry 42 and sensor signal processing circuitry 44. Sensor drive circuitry 42 includes DC source conditioning circuitry 48, oscillator 50, and Wheatstone bridge 52. Sensor signal processing circuitry 44 includes Wheatstone bridge 52, instrumentation amplifier 54, filtering and output adjustment circuitry 56, and temperature compensation circuitry 58. Wheatstone bridge 52 includes terminals 62, 64, 66, and 68, terminals 66 and 68 being connected to electrodes 22A and 22B, respectively, of conductivity cell 10, and resistors R1, R2, and R3. Also shown in FIG. 2 is resistance Rx (which is the resistance between electrodes 22A and 22B), input DC voltage $V_{IN}$, and output DC voltage $V_{OUT}$.

Circuitry 40 provides an AC current input through conductivity cell 10 via sensor drive circuitry 42 and provides conductivity cell 10 with sensor signal processing circuitry 44. Sensor drive circuitry 42 is powered by input DC voltage source $V_{IN}$, which is provided to DC source conditioning circuitry 48. DC source conditioning circuitry 48 conditions DC voltage $V_{IN}$ in order to provide conditioned DC supply voltage to oscillator 50. AC drive voltage from oscillator 50 is supplied to terminals 62 and 66 of Wheatstone bridge 52. Terminals 68 and 66 of Wheatstone bridge 52 are connected to electrodes 22A and 22B of conductivity cell 10. Wheatstone bridge 52 provides AC drive current to electrodes 22A and 22B. As such, electrodes 22A and 22B are current or drive electrodes. Wheatstone bridge 52 is also connected to sensor signal processing circuitry 44 via instrumentation amplifier 54. Instrumentation amplifier 54 is connected to terminals 64 and 68 of Wheatstone bridge 52. As such, electrodes 22A and 22B also function as voltage sensing electrodes. Wheatstone bridge 52 provides the connection of electrodes 22A and 22B to both sensor drive circuitry 42 and sensor signal processing circuitry 44. Instrumentation amplifier 54 receives a sensor signal, in the form of voltage between terminals 64 and 68, from Wheatstone bridge 52 and amplifies the sensor signal. The amplified sensor signal is supplied to filtering and output adjustment circuitry 56. Instrumentation amplifier 54 also provides feedback to oscillator 50 to automatically adjust the drive voltage of oscillator 50 based on the sensor signal, thus varying the amplitude of the AC drive voltage to terminal 62 and 68 of Wheatstone bridge 52. Filtering and output adjustment circuitry 56 filters and adjusts the amplified sensor signal, which is then supplied to temperature compensation circuitry 58. Temperature compensation circuitry 58 compensates for temperature based on temperature sensor signals from thermistors in electrodes 22A and 22B. Temperature sensor signals are a function of the temperature of each of electrodes 22A and 22B. The output of temperature compensation circuitry 58 is a temperature compensated sensor signal, which is output DC voltage $V_{OUT}$. Output DC voltage $V_{OUT}$ is a function of the conductivity of the fluid in conductivity cell 10.

Wheatstone bridge 52 has terminals 62, 64, 66, and 68. Terminals 62 and 66 are drive terminals and receive AC drive voltage from oscillator 50, and terminals 64 and 68 are sensor terminals and provide sensor signals from electrodes 22A and 22B to instrumentation amplifier 54. Wheatstone bridge 52 has resistors R1, R2, R3, and Rx. R1 is between terminals 62 and 64. R2 is between terminals 64 and 66. R3 is between terminals 62 and 68. Rx is between terminals 66 and 68. R1, R2, and R3 are all of known resistance. Rx is the resistance of the fluid in flow-through hole 30 between electrodes 22A and 22B, which is the inverse of the conductivity of the fluid. Resistors R1 and R2 make up a first leg of Wheatstone bridge 52, and resistors R3 and Rx make up a second leg of Wheatstone bridge 52.

The AC drive voltage from oscillator 50 provides an AC drive to both the first leg and the second leg of Wheatstone bridge 52. Because electrodes 22A and 22B are in contact with the fluid in flow-through hole 30, electrodes 22A and 22B deliver the current to or energize or provide excitation to the fluid.

Sensor signal processing circuitry 44 measures the voltage of the fluid, due to the induced current, between electrodes 22A and 22B. The difference in voltage between terminals 64 and 68 connected to instrumentation amplifier 54 makes up the sensor signal received by instrumentation amplifier 54. The sensor signal allows instrumentation amplifier 54 and other components of sensor signal processing circuitry 44 to provide output DC voltage $V_{OUT}$, which is a function of the voltage between terminals 64 and 68, which in turn is a function of Rx, the resistance between electrodes 22A and 22B.

AC voltage is used to deliver current to electrode pair 22A, 22B via Wheatstone bridge 52 to avoid any polarization or hydrolysis of the fluid flowing through conductivity cell 10, which would impede an accurate measurement. Wheatstone bridge 52 sets a desirable current to flow through electrodes 22A and 22B so that electrodes 22A and 22B can deliver a voltage that is a function of conductivity of the fluid flowing through conductivity cell 10.

Figure 3A:
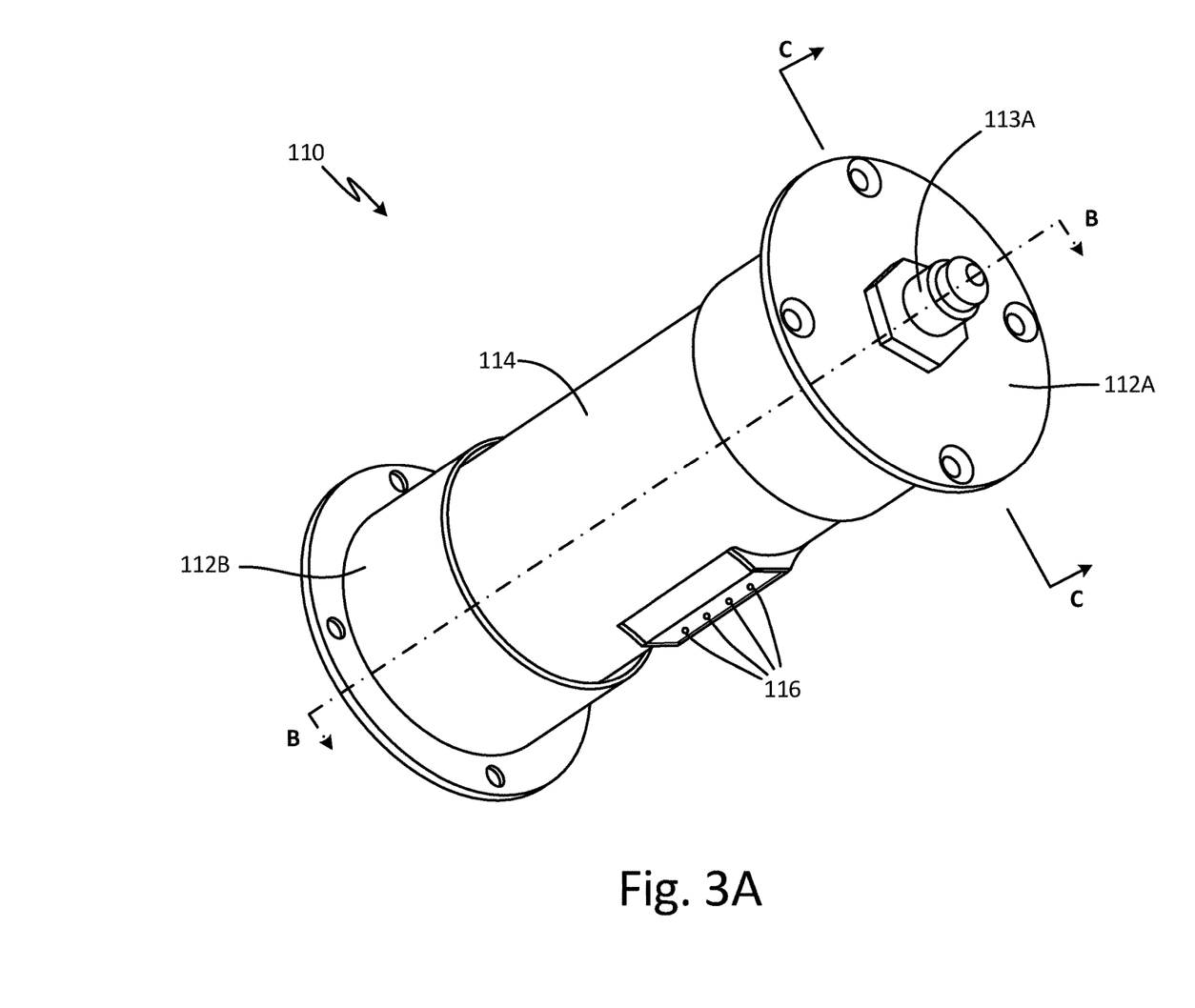
FIG. 3A is an isometric view of a second embodiment of a conductivity cell.

FIG. 3A is an isometric view of a second embodiment of conductivity cell 110. Conductivity cell 110 includes first end fitting 112A with inlet nipple 113A and second end fitting 112B with outlet nipple 113B (shown in FIG. 3B), flow tube holder 114, and electrical wiring holes 116.

End fittings 112A, 112B are positioned on cylindrical flow tube holder 114. First end fitting 112A has inlet nipple 113A and is positioned on a first end of flow tube holder 114, and second end fitting 112B has outlet nipple 113B and is positioned on a second end of flow tube holder 114. End fittings 112A, 112B are connected via inlet nipple 113A and outlet nipple 113B to a fluid line (not shown) containing a fluid to be measured. End fittings 112A, 112B are made of stainless steel. Flow tube holder 114 is made of plastic. Electrical wiring holes 116 are passageways extending from an interior of flow tube holder 114 to an exterior of flow tube holder 114. Conductivity cell 110 has four electrical wiring holes 116.

Ending fittings 112A, 112B connect conductivity cell 110 to a fluid line (not shown) such that conductivity cell 110 in installed in-line with the fluid. Conductivity cell 110 is also connected to circuitry via wires, which exit flow tube holder 114 of conductivity cell 110 through electrical wiring holes 116. Conductivity cell 110 measures the conductivity of the fluid in the fluid line. The conductivity measurement indicates the ionic make-up of the fluid or how dirty the fluid is.

Figure 3B:
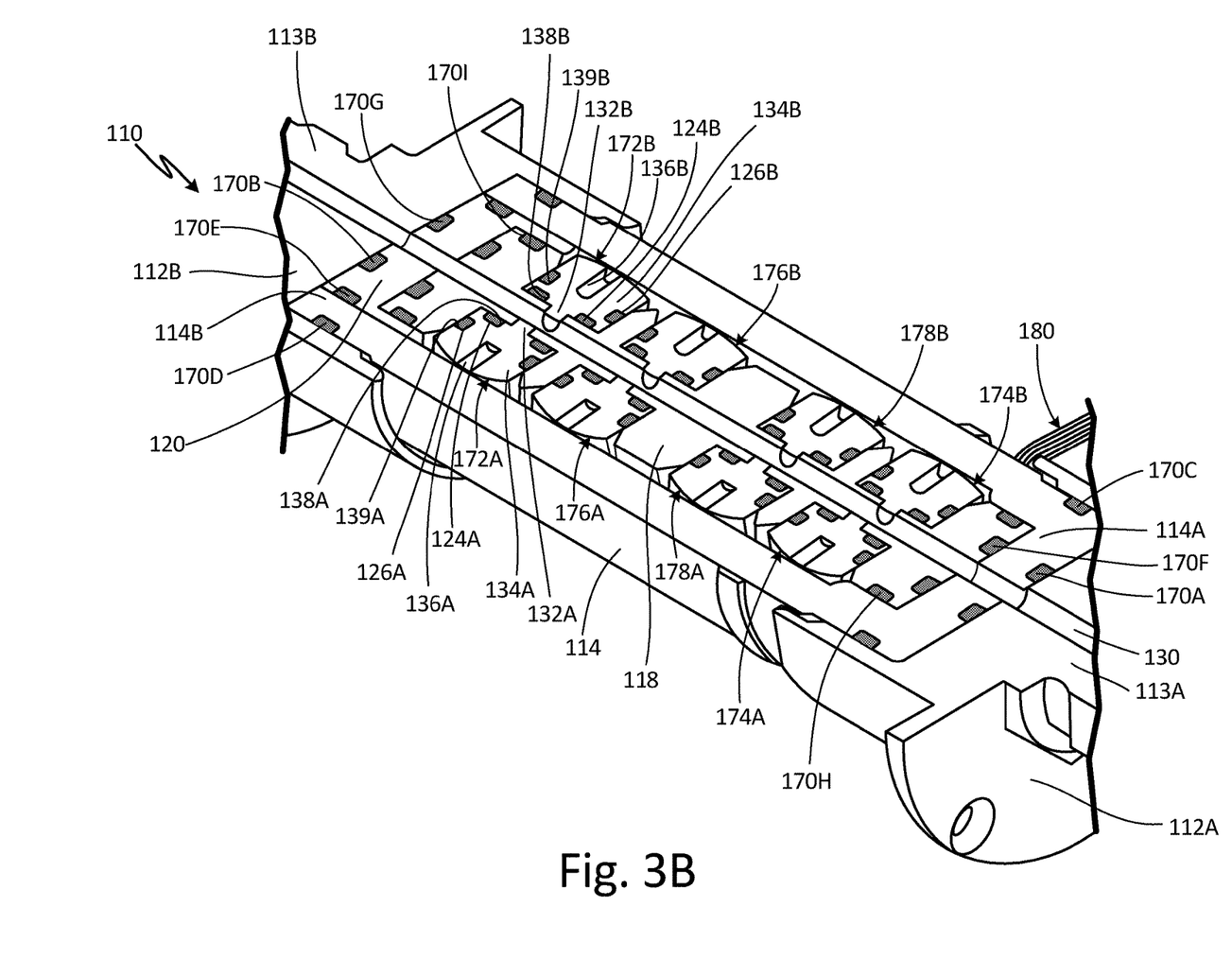
FIG. 3B is a partial isometric cross-sectional view of the second embodiment of the conductivity cell taken along line B-B of FIG. 3A.
Figure 3C:
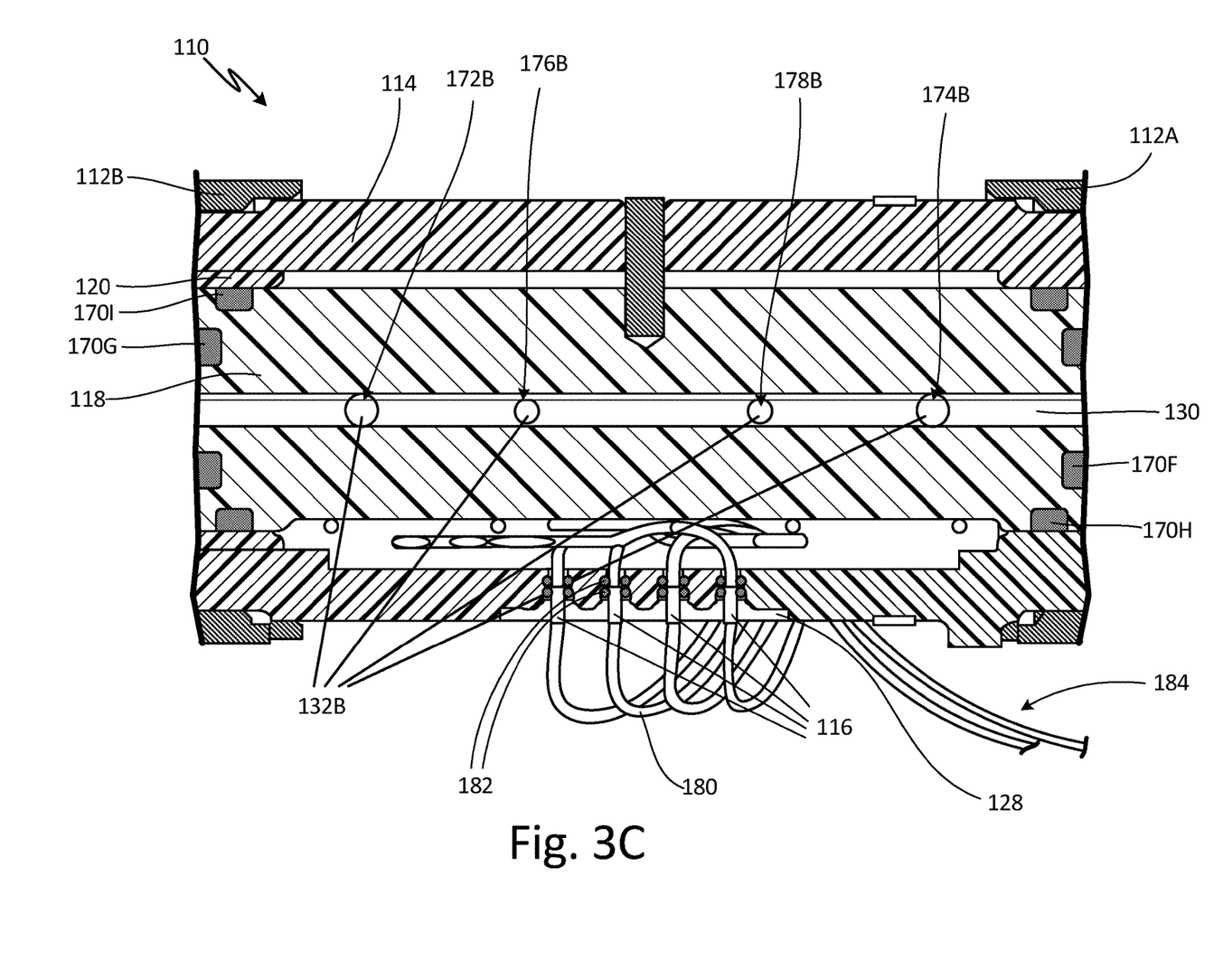
FIG. 3C is a partial cross-sectional view of the second embodiment of the conductivity cell taken along line C-C of FIG. 3A.

FIG. 3B is a partial isometric cross-sectional view of the second embodiment of conductivity cell 110 taken along line B-B of FIG. 3A. FIG. 3C is a partial cross-sectional view of the second embodiment of the conductivity cell 110 taken along line C-C of FIG. 3A. FIGS. 3B and 3C will be discussed together. In addition to the elements shown in FIG. 3A, conductivity cell 110 includes flow tube holder 114 having first end 114A and second end 114B, flow tube 118, end cap 120, o-rings 170A, 170B, 170C, 170D, 170E, 170F, 170G, 170H, and 170I, electrode pair 172A (shown in FIG. 3B), 172B, electrode pair 174A (shown in FIG. 3B), 174B, electrode pair 176A (shown in FIG. 3B), 176B, electrode pair 178A (shown in FIG. 3B), 178B, face o-rings 124A and 124B (shown in FIG. 3B), rod o-rings 126A and 126B (shown in FIG. 3B), wires 180, o-rings 182 (shown in FIG. 3C), epoxy 128 (shown in FIG. 3C), flow-through hole 130, and wires 184 (shown in FIG. 3C). Electrodes 172A, 172B, 174A, 174B, 176A, 176B, 178A, and 178B include stems 132A and 132B, main bodies 134A and 134B (shown in FIG. 3B), holes 136A and 136B (shown in FIG. 3B), grooves 138A and 138B (shown in FIG. 3B), and grooves 139A and 139B (shown in FIG. 3B), respectively.

Flow tube holder 114 has first end 114A that is closed and second end 114B that is open. Flow tube 118 is press-fit into flow tube holder 114 through open second end 114B of flow tube holder 114 such that flow tube holder 114 surrounds flow tube 118. Flow tube 118 is made of plastic. Mating faces of flow tube holder 114 and flow tube 118 are glued together with epoxy. End cap 120 is press-fit into open second end 114B of flow tube holder 114 such that it is positioned adjacent flow tube 118 and second end fitting 112B. End cap 120 is positioned to seal off open second end 114B of flow tube holder 114. End cap 120 is glued to flow tube holder 114. End cap 120 is made of plastic.

O-ring 170A is a face o-ring positioned at first end 114A of flow tube holder 114 and adjacent first end fitting 112A. O-ring 170B is a face o-ring positioned at end cap 120 and adjacent second end fitting 112B. O-ring 170C is a circumferential o-ring positioned around first end 114A of flow tube holder 114 and adjacent first end fitting 112A. O-ring 170D is a circumferential o-ring positioned around second end 114B of flow tube holder 114 and adjacent second end fitting 112B. O-ring 170E is a circumferential o-ring positioned around end cap 120 and adjacent second end 114B of flow tube holder 114. O-ring 170F is a face o-ring positioned at a first end of flow tube 118 and adjacent first end 114A of flow tube 114. O-ring 170G is a face o-ring positioned at a second end of flow tube 118 and adjacent end cap 120. O-ring 170H is a circumferential o-ring positioned around a first end of flow tube 118 and adjacent first end 114A of flow tube 114. O-ring 170I is a circumferential o-ring positioned around a second end of flow tube 118 and adjacent end cap 120.

Electrode pair 172A, 172B, electrode pair 174A, 174B, electrode pair 176A, 176B, and electrode pair 178A, 178B are seated in flow tube 118. More specifically, electrodes 172A, 172B, 174A, 174B, 176A, 176B, 178A, and 178B are press-fit into flow tube 118 before flow tube 118 is press-fit into flow tube holder 114. Flow tube holder 114 has an inner diameter sized to ensure electrodes 172A, 172B, 174A, 174B, 176A, 176B, 178A, and 178B remain properly pressed into flow tube 118, outer ends of electrodes 172A, 172B, 174A, 174B, 176A, 176B, 178A, and 178B being in contact with an inner wall of flow tube holder 114. Flow tube 114 press-fits electrodes 172A, 172B, 174A, 174B, 176A, 176B, 178A, and 178B to control the axial and radial positions of electrodes 172A, 172B, 174A, 174B, 176A, 176B, 178A, and 178B. Electrodes 172A, 172B, 174A, 174B, 176A, 176B, 178A, and 178B are made of nickel alloy. Conductivity cell 110 has four electrode pairs 172A, 172B; 174A, 174B; 176A, 176B; and 178A, 178B, each with one electrode 172A, 174A, 176A, and 178A in a first side of flow tube 118 and one electrode 172B, 174B, 176B, and 178B in a second side of flow tube 118. Conductivity cell 110 has eight electrodes 172A, 172B, 174A, 174B, 176A, 176B, 178A, and 178B.

Face o-rings 124A and 124B and rod o-rings 126A and 126B are positioned on each of electrodes 172A, 172B, 174A, 174B, 176A, 176B, 178A, and 178B, respectively. Face o-rings 124A and 124B and rod o-rings 126A and 126B contact electrodes 172A, 172B, 174A, 174B, 176A, 176B, 178A, and 178B, respectively, and flow tube 118. First ends of wires 180 are connected via brazing to electrodes 172A, 172B, 174A, 174B, 176A, 176B, 178A, and 178B, respectively. Wires 180 exit flow tube holder 114 through electrical wiring holes 116 such that second ends of wires 180 are located outside flow tube holder 114. O-rings 182 are positioned around wires 180 in electrical wiring holes 116, two o-rings 182 being positioned in each electrical wiring hole 116. Epoxy 128 is positioned in electrical wiring holes 116 adjacent wires 180 and o-rings 182. Epoxy 128 fills in each electrical wiring hole 116 such that epoxy 128 is flush with an exterior surface of flow tube holder 114.

Flow-through hole 130 extends through conductivity cell 110 from first end fitting 112A to second end fitting 112B. Flow-through hole 130 is formed by inner diameters of first end fitting 112A, a first end 114B of flow tube holder 114, flow tube 118, electrodes 172A, 172B, 174A, 174B, 176A, 176B, 178A, and 178B, end cap 120, and second end fitting 112B.

Each of electrodes 172A, 172B, 174A, 174B, 176A, 176B, 178A, and 178B has a similar structure. The components of electrodes 172A, 172B, 174A, 174B, 176A, 176B, 178A, and 178B are the same and will be described with reference to electrode 172A. Electrode 172A has cylindrical stem 132A extending from an inner end of main body 134A to flow-through hole 130. Stem 132A extends through flow tube 118 such that an inner end of stem 132A is flush with the inner diameter of flow tube 118. Stem 132A is positioned to be in contact with fluid in flow-through hole 130. Electrode 172A has hole 136A extending into a center of main body 134A from an outer end of main body 134A. Hole 136A holds a thermistor (not shown) in electrode 172A. A wire 184 connects the thermistor in electrode 172A to circuitry 140 (shown in FIG. 4). In alternate embodiments, electrode 172A does not include hole 136A. Main body 134A of electrode 172A has annular grooves 138A and 139A. Groove 138A is located in the inner end of main body 134A, and groove 139A is located around main body 134A between the inner end of main body 134A and the outer end of main body 134A. Groove 138A is configured to receive face o-ring 124A and groove 139A is configured to receive rod o-ring 126A. As such, face o-ring 124A is positioned around stem 132A of electrode 172A, and rod o-ring 126A is positioned around main body 134A of electrode 172A. In alternate embodiments, electrodes 172A, 172B, 174A, 174B, 176A, 176B, 178A, and 178B can be sized and shaped to correspond to the desired operating point of conductivity.

Flow tube holder 114, flow tube 118, and end cap 120 have initial inner diameters smaller than the desired diameter of flow-through hole 130. Stems 132A and 132B of electrodes 172A, 172B, 174A, 174B, 176A, 176B, 178A, and 178B are initially longer than desired such that stems 132A and 132B protrude into flow-through hole 130. After the conductivity cell 110 has been assembled, epoxied together, and cured, flow-through hole 130 is reamed out to yield a final desired diameter of flow-through hole 130. After flow-through hole 130 has been reamed out, ends of stems 132A and 132B making up flow-through hole 130 are curved and concave as they are flush with the inner diameter of flow tube 118. End fittings 112A and 112B have inner diameters equal to the desired diameter of flow-through hole 130 and do not get reamed out.

Ending fittings 112 connect conductivity cell 110 to a fluid line (not shown) such that conductivity cell 110 in installed in-line with the fluid. Fluid from the fluid line runs through conductivity cell 110 through flow-through hole 130. O-rings 170A and 170C provide sealing between first end 114A of flow tube holder 114 and first end fitting 112A. O-ring 170B provides sealing between end cap 120 and second end fitting 112B. O-ring 170D provides sealing between second end 114B of flow tube holder 114 and second end fitting 112B. O-ring 170E provides sealing between end cap 120 and second end 114B of flow tube holder 114. O-rings 170F and 170H provide sealing between the first end of flow tube 118 and first end 114A of flow tube 114. O-rings 170G and 170I provide sealing between the second end of flow tube 118 and end cap 120. Face o-rings 124A and 124B and rod o-rings 126A and 126B provide sealing between flow tube 118 and electrodes 172A, 172B, 174A, 174B, 176A, 176B, 178A, and 178B. Flow tube holder 114, flow tube 118, and end cap 120 are plastic so that electrodes 172A, 172B, 174A, 174B, 176A, 176B, 178A, and 178B are the only metal in contact with fluid in flow-through hole 130 in flow tube holder 114. Fluid in flow-through hole 130 is energized by electrode pairs 172A, 172B and 174A, 174B, and the resistance of the fluid between electrode pairs 176A, 176B and 178A, 178B is measured by electrode pairs 176A, 176B and 178A, 178B. Wires 180 connected to electrodes 172A, 172B, 174A, 174B, 176A, 176B, 178A, and 178B connect electrode pairs 172A, 172B; 174A, 174B; 176A, 176B; and 178A, 178B to external circuitry required for electrodes 172A, 172B, 174A, 174B to energize the fluid and for electrodes 176A, 176B, 178A, and 178B to measure the resistance of the fluid. Wires 180 exit flow tube holder 114 through electrical wiring holes 116 and open centers of o-rings 182, which center wires 180 as they exit electrical wiring holes 116 to reach the external circuitry. Epoxy 128 fills in electrical wiring holes 116 to secure and support wires 180 as they exit flow tube holder 114, to seal flow tube holder 114 from leakage, and to secure flow tube 118 from creeping, rotating, or moving.

Reaming to create flow-through hole 130 ensures electrodes 172A, 172B, 174A, 174B, 176A, 176B, 178A, and 178B are properly distanced with a high degree of precision. Reaming also ensures flow tube 118, flow tube holder 114, and end cap 120 all have the same inner diameters and ensures that flow-through hole 130 is smooth and continuous. As a result, flow-through hole 130 does not include edges where a bubble from fluid in flow-through hole 130 could collect. Electrodes 172A, 172B, 174A, 174B, 176A, 176B, 178A, and 178B are press-fit into flow tube 118 and flow tube 118 is press-fit into flow tube holder 114 to yield proper squeeze and engagement of face o-rings 124A and 124B on stems 132A and 132B of electrodes 172A, 172B, 174A, 174B, 176A, 176B, 178A, and 178B, respectively, and proper axial and radial positioning of electrodes 172A, 172B, 174A, 174B, 176A, 176B, 178A, and 178B. Face o-rings 124A and 124B and rod o-rings 126A and 126B provide water-tight sealing between flow tube 118 and electrodes 172A, 172B, 174A, 174B, 176A, 176B, 178A, and 178B to ensure the fluid in flow-through hole 130 does not leak past electrodes 172A, 172B, 174A, 174B, 176A, 176B, 178A, and 178B, respectively, and into other internal components of conductivity cell 110. The design of conductivity cell 110 also makes it easy to manufacture.

Figure 4:
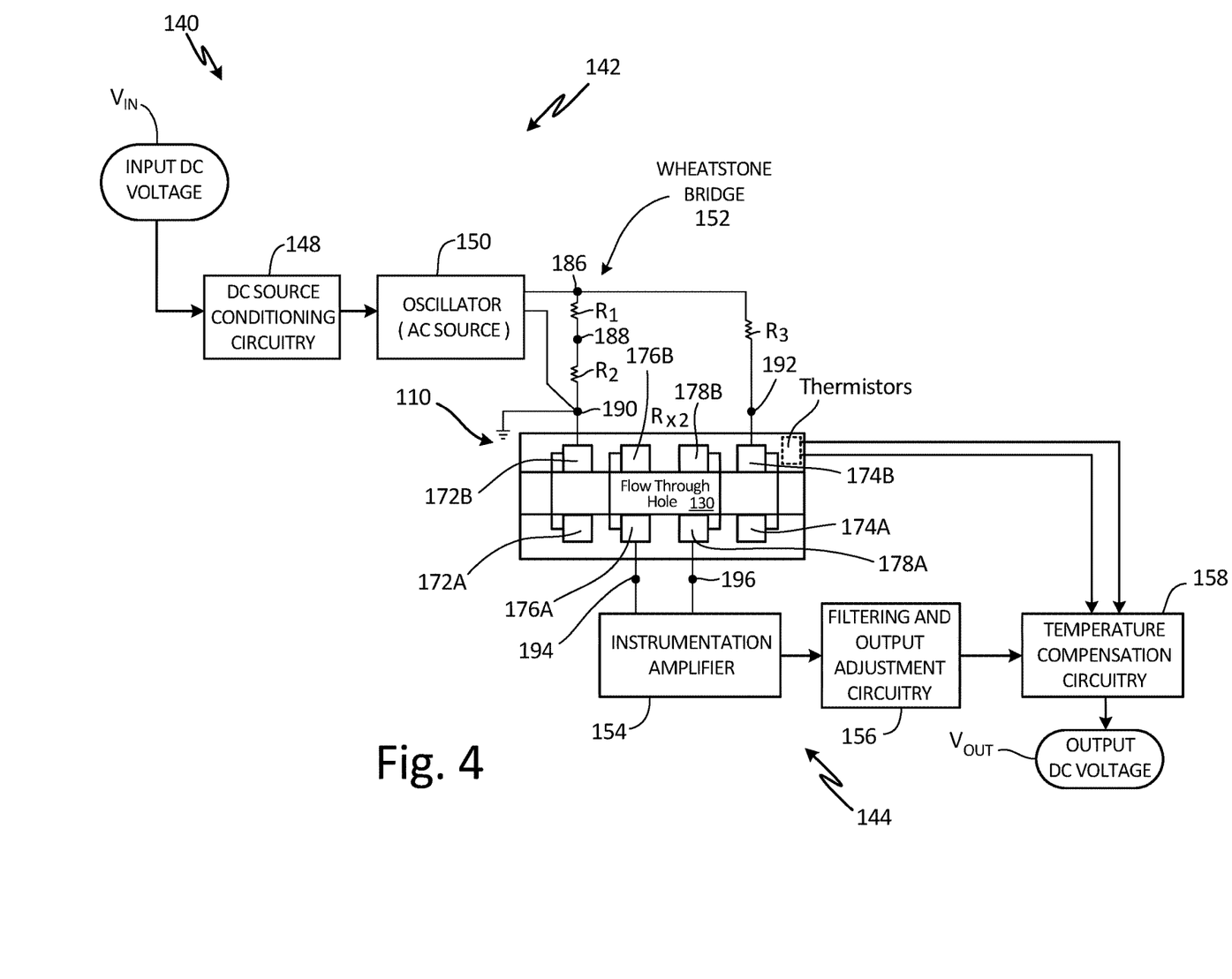
FIG. 4 is a block diagram showing a circuitry connected to the conductivity cell.

FIG. 4 is a block diagram showing circuitry 140 connected to conductivity cell 110. Conductivity cell 110 includes electrode pair 172A, 172B, electrode pair 174A, 174B, electrode pair 176A, 176B, electrode pair 178A, 178B, and flow-through hole 130. Circuitry 140 includes sensor drive circuitry 142 and sensor signal processing circuitry 144. Sensor drive circuitry 142 includes DC source conditioning circuitry 148, oscillator 150, and Wheatstone bridge 152. Sensor signal processing circuitry 44 includes instrumentation amplifier 154, filtering and output adjustment circuitry 156, and temperature compensation circuitry 158. Wheatstone bridge 152 includes terminals 186, 188, 190, and 192 and resistors R1, R2, and R3. Terminals 190 and 192 are connected to electrode pairs 172A, 172B and 174A, 174B, respectively, of conductivity cell 110. Instrumentation amplifier includes terminals 194 and 196, which are connected to electrode pairs 176A, 176B and 178A, 178B, respectively, of conductivity cell 10. Also shown in FIG. 4 is $Rx_2$, input DC voltage $V_{IN}$, and output signal $V_{OUT}$.

Electrodes 172A and 172B are connected together, electrodes 174A and 174B are connected together, electrodes 176A and 176B are connected together, and electrodes 178A and 178B are connected together. Electrodes 172A, 174A, 176A, and 178A are positioned on a first side of flow-through hole 130 of conductivity cell 110 and electrodes 172B, 174B, 176B, and 178B are positioned on a second side of flow-through hole 130 such that electrodes 172A and 172B are opposing each other, electrodes 174A and 174B are opposing each other, electrodes 176A and 176B are opposing each other, and electrodes 178A and 178B are opposing each other. Electrode pair 172A, 172B is positioned at a first end of flow-through hole 130 and electrode pair 174A, 174B is positioned at a second end of flow-through hole 130, which extends through conductivity cell 110. Electrode pair 176A, 176B and electrode pair 178A, 178B are positioned along a length of flow-through hole 130 between electrode pairs 172A, 172B and 174A, 174B. As such, electrode pairs 172A, 172B and 174A, 174B are outer electrode pairs and electrode pairs 176A, 176B and 178A, 178B are inner electrode pairs. Electrodes 172A, 172B, 174A, 174B, 176A, 176B, 178A, and 178B are all positioned to be in contact with fluid in flow-through hole 130.

Circuitry 140 provides an AC current input through conductivity cell 110 via sensor drive circuitry 142. Conductivity cell 110 produces a sensor signal that is a function of the conductivity of fluid between electrode pairs 176A, 176B and 178A, 178B via sensor signal processing circuitry 144. Sensor drive circuitry 142 is powered by input DC voltage $V_{IN}$, which is provided to DC source conditioning circuitry 148. DC source conditioning circuitry 148 conditions DC voltage in order to provide conditioned DC supply voltage to oscillator 150. Oscillator 150 produces an AC drive voltage that is supplied to terminals 186 and 190 to drive Wheatstone bridge 152. Wheatstone bridge 152 is connected to electrode pair 172A, 172B and electrode pair 174A, 174B at terminals 190 and 192, respectively. Wheatstone bridge 152 provides AC drive current to electrodes 172A, 172B, 174A, and 174B. As such, electrodes 172A, 172B, 174A, and 174B are current or drive electrodes. Wheatstone bridge 152 is not connected to instrumentation amplifier 154. Further, Wheatstone bridge 152 is not connected to electrodes 176A, 176B, 178A, and 178B.

Instrumentation amplifier 154 is connected to electrode pair 176A, 176B and electrode pair 178A, 178B to receive the sensor signal, which is voltage that is a function of resistance, and therefore conductivity, of the fluid between electrode pairs 176A, 176B and 178A, 178B. As such, electrodes 176A, 176B, 178A, and 178B are voltage or sensor electrodes. Instrumentation amplifier 154 is not connected to electrodes 172A, 172B, 174A, and 174B. Instrumentation amplifier 154 receives and amplifies the sensor signal. The amplified sensor signal is supplied to filtering and output adjustment circuitry 156. Filtering and output adjustment circuitry 156 filters and adjusts the amplified sensor signal, which is then supplied to temperature compensation circuitry 158. Temperature compensation circuitry 158 compensates for temperature based on temperature sensor signals from thermistors in electrodes 172A, 172B, 174A, 174B, 176A, 176B, 178A, and 178B. Temperature sensor signals are a function of the temperature of each of electrodes 172A, 172B, 174A, 174B, 176A, 176B, 178A, and 178B. The output of temperature compensation circuitry 158 is a temperature compensated sensor signal, which is output DC voltage $V_{OUT}$. Output DC voltage $V_{OUT}$ is delivered as an output signal that represents the conductivity of the fluid in conductivity cell 110.

Wheatstone bridge 152 has terminals 186, 188, 190, and 192. Terminals 186 and 190 are drive terminals and receive AC drive voltage from oscillator 150. None of terminals 186, 188, 190, and 192 are connected to instrumentation amplifier 154. Wheatstone bridge 152 has resistors R1, R2, and R3. R1 is between terminals 186 and 188. R2 is between terminals 188 and 190. R3 is between terminals 186 and 192. R1, R2, and R3 are all of known resistance. $Rx_2$ is the resistance formed by current electrodes 172A, 172B, 174A, and 174B and fluid within flow through hole 130 of conductivity cell 110. Resistors R1 and R2 make up a first leg of Wheatstone bridge 152, and resistor R3 and $Rx_2$ make up a second leg of Wheatstone bridge 152. Instrumentation amplifier 154 has terminal 194 connected to electrode pair 176A, 176B and terminal 196 connected to electrode pair 178A, 178B.

The AC drive voltage from oscillator 150 provides an AC drive to both the first leg and the second leg of Wheatstone bridge 152. Because electrodes 172A, 172B, 174A, and 174B are in contact with the fluid in flow through hole 130, current electrodes 172A, 172B, 174A, and 174B deliver current to or energize or provide excitation to the fluid.

Sensor signal processing circuitry 144 measures the voltage between electrode pairs 176A, 176B and 178A, 178B due to the current induced by electrode pairs 172A, 172B and 174A, 174B. Terminal 194 is connected to electrode pair 176A, 176B and to instrumentation amplifier 154. Terminal 196 is connected to electrode pair 178A, 178B and to instrumentation amplifier 154. The difference in voltage between electrode pairs 176A, 176B and 178A, 178B is the sensor signal received by instrumentation amplifier 154.

AC voltage is used to deliver current to electrode pairs 172A, 172B and 174A, 174B via Wheatstone bridge 152 to avoid any polarization or hydrolysis of the fluid flowing through conductivity cell 110, which would impede an accurate measurement.

Instrumentation amplifier 154 is connected to voltage electrodes 176A, 176B, 178A, and 178B so that electrodes 176A, 176B, 178A, and 178B can measure the voltage of the fluid due to the current induced by electrode pairs 172A, 172B and 174A, 174B. Filtering and output adjustment circuitry 156 provides a desirable DC output voltage range. Ohm's law is used with output DC voltage $V_{OUT}$ to determine the resulting conductance or inverse resistance of the fluid at room temperature. More specifically, conductivity of the fluid or liquid solution is a function of the conductance or resistance sensed by electrode pairs 176A, 176B and 178A, 178B. The conductance or resistance between electrode pairs 176A, 176B and 178A, 178B is also a function of a distance between electrode pairs 176A, 176B and 178A, 178B and a surface area of electrodes 176A, 176B, 178A, and 178B. This geometric relationship is the cell constant. The conductivity measurement indicates the ionic make-up of the fluid or how dirty the fluid is.

Positioning of electrode pairs 172A, 172B; 174A, 174B; 176A, 176B; and 178A, 178B with each pair connected together and on opposing sides of flow-through hole 130 enables the application of current to both sides of flow-through hole 130 such that the fluid is energized evenly on both sides. As a result, the voltage is more uniform. Additionally, measurement of voltage comes from both sides of flow-through hole 130. Such an arrangement increases the stability and sensitivity, and therefore accuracy, of the conductivity measurement.

Wheatstone bridge 152 being connected to current electrode pairs 172A, 172B and 174A, 174B and instrumentation amplifier 154 being connected to voltage electrode pairs 176A, 176B and 178A, 178B, with current electrode pairs 172A, 172B and 174A, 174B not being physically connected to voltage electrode pairs 176A, 176B and 178A, 178B other than through the fluid in flow-through hole 130, results in high accuracy of the conductivity measurement near the desired operating point of conductivity.

Discussion of Possible Embodiments

The following are non-exclusive descriptions of possible embodiments of the present invention.

A conductivity cell includes a cylindrical flow tube holder having a closed first end and an open second end; a first end fitting positioned on the first end of the flow tube holder, a second end fitting positioned on the second end of the flow tube holder; a flow tube positioned within the flow tube holder; an end cap positioned in the open second end of the flow tube holder and adjacent the flow tube and the second end fitting; a plurality of electrodes positioned in the flow tube; a plurality of o-rings positioned on the electrodes; and a flow through hole extending from the first end fitting through the flow tube holder, the flow tube, and the end cap to the second end fitting; wherein the plurality of electrodes are press-fit into the flow tube.

The conductivity cell of the preceding paragraph can optionally include, additionally and/or alternatively, any one or more of the following features, configurations and/or additional components:

The flow tube is press-fit into the flow tube holder.

The external surface of the flow tube and the internal surface of the flow tube holder are glued together with epoxy.

The inner diameter of the flow tube holder is configured to control the axial and radial positions of the electrodes in the flow tube.

The end cap is press fit in the second end of the flow tube holder.

The first end fitting and the second end fitting are configured to connect to a fluid line.

Each electrode of the plurality of electrodes has at least one groove configured to receive an o-ring of the plurality of o-rings.

Each electrode of the plurality of electrodes includes a cylindrical stem extending from an inner end of a main body of the electrode to the flow through hole.

Each electrode of the plurality of electrodes includes a groove on the inner end of the main body of the electrode, wherein the groove surrounds the stem and is configured to receive an o-ring of the plurality of o-rings.

Each electrode of the plurality of electrodes includes a groove extending around a side of the main body of the electrode, the side being between the inner end of the main body and the outer end of main body, wherein the groove is configured to receive an o-ring of the plurality of o-rings.

The flow through hole is a smooth surface.

The conductivity cell includes two electrodes.

The conductivity cell includes eight electrodes.

A conductivity cell includes a cylindrical flow tube holder having a closed first end and an open second end; a first end fitting positioned on the first end of the flow tube holder; a second end fitting positioned on the second end of the flow tube holder; a flow tube positioned within the flow tube holder; an end cap positioned in the open second end of the flow tube holder and adjacent the flow tube and the second end fitting; a plurality of electrodes positioned in the flow tube, each electrode including: a main body; a stem extending from an inner end of a main body; a groove on the inner end of the main body of the electrode, the groove surrounding the stem; a groove extending around a side of the main body, the side located between the inner end of the main body and an outer end of main body; an o-ring positioned in each of the grooves on the electrodes; and a flow through hole extending from the first end fitting through the flow tube holder, the flow tube, and the end cap to the second end fitting; wherein the plurality of electrodes are press-fit into the flow tube.

The conductivity cell of the preceding paragraph can optionally include, additionally and/or alternatively, any one or more of the following features, configurations and/or additional components:

The flow tube is press-fit into the flow tube holder.

The inner diameter of the flow tube holder is configured to control the axial and radial positions of the electrodes in the flow tube.

The end cap is press fit in the second end of the flow tube holder.

The flow through hole is a smooth surface.

The first end fitting and the second end fitting are configured to connect to a fluid line.

A conductivity cell includes a cylindrical flow tube holder having a closed first end and an open second end; a first end fitting positioned on the first end of the flow tube holder; a second end fitting positioned on the second end of the flow tube holder, a flow tube positioned within the flow tube holder, an end cap positioned in the open second end of the flow tube holder and adjacent the flow tube and the second end fitting; a plurality of electrodes positioned in the flow tube; a plurality of o-rings positioned on the electrodes; and a flow through hole extending from the first end fitting through the flow tube holder, the flow tube, and the end cap to the second end fitting; wherein the flow tube is press fit into the flow tube holder.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A conductivity cell comprising:
  a cylindrical flow tube holder having a closed first end and an open second end;
  a first end fitting positioned on the first end of the flow tube holder;
  a second end fitting positioned on the second end of the flow tube holder;
  a flow tube positioned within the flow tube holder, the flow tube having a plurality of cavities;
  an end cap positioned in the open second end of the flow tube holder and adjacent the flow tube and the second end fitting;
  a plurality of electrodes positioned in the flow tube;
  a plurality of o-rings positioned on the electrodes; and
  a flow through hole extending from the first end fitting through the flow tube holder, the flow tube, and the end cap to the second end fitting;
  wherein each of the plurality of electrodes is positioned in a corresponding one of the plurality of cavities such that a press-fit engagement is formed between each electrode in each corresponding cavity of the flow tube; and
  wherein outer ends of the electrodes are in contact with an inner wall of the flow tube holder and inner ends of the electrodes form part of the flow through hole.

2. The conductivity cell of claim 1 wherein the flow tube holder defines a cavity and the flow tube is positioned within the flow tube holder cavity such that a press-fit engagement is formed between the flow tube holder and the flow tube.

3. The conductivity cell of claim 2 wherein the external surface of the flow tube and the internal surface of the flow tube holder are glued together with epoxy.

4. The conductivity cell of claim 1 wherein the inner diameter of the flow tube holder is configured to control the axial and radial positions of the electrodes in the flow tube.

5. The conductivity cell of claim 1 wherein the end cap is positioned in the open second end of the flow tube holder such that a press-fit engagement is formed between the end cap and in the second end of the flow tube holder.

6. The conductivity cell of claim 1 wherein the first end fitting and the second end fitting are configured to connect to a fluid line.

7. The conductivity cell of claim 1 wherein each electrode of the plurality of electrodes has at least one groove configured to receive an o-ring of the plurality of o-rings.

8. The conductivity cell of claim 1 wherein each electrode of the plurality of electrodes includes a cylindrical stem extending from an inner end of a main body of the electrode to the flow through hole.

9. The conductivity cell of claim 8 wherein each electrode of the plurality of electrodes includes a groove on the inner end of the main body of the electrode, wherein the groove surrounds the stem and is configured to receive an o-ring of the plurality of o-rings.

10. The conductivity cell of claim 9 wherein each electrode of the plurality of electrodes includes a groove extending around a side of the main body of the electrode, the side being between the inner end of the main body and the outer end of main body, wherein the groove is configured to receive an o-ring of the plurality of o-rings.

11. The conductivity cell of claim 1 wherein the flow through hole is a smooth surface.

12. The conductivity cell of claim 1 wherein the conductivity cell includes two electrodes.

13. The conductivity cell of claim 1 wherein the conductivity cell includes eight electrodes.

14. A conductivity cell comprising:
a cylindrical flaw tube holder having a closed first end and an open second end;
a first end fitting positioned on the first end of the flow tube holder;
a second end fitting positioned on the second end of the flow tube holder;
a flow tube positioned within the flow tube holder, the flow tube having a plurality of cavities;
an end cap positioned in the open second end of the flow tube holder and adjacent the flow tube and the second end fitting;
a plurality of electrodes positioned in the flow tube, each electrode including:
a main body;
a stem extending from an inner end of the main body;
a groove on the inner end of the main body of the electrode, the groove surrounding the stem;
a groove extending around a side of the main body, the side located between the inner end of the main body and an outer end of the main body;
an o-ring positioned in each of the grooves on the electrodes; and
a flow through hole extending from the first end fitting through the flow tube holder, the flow tube, and the end cap to the second end fitting;
wherein each of the plurality of electrodes is positioned in a corresponding one of the plurality of cavities such that a press-fit engagement is formed between each electrode in each corresponding cavity of the flow tube.

15. The conductivity cell of claim 14, wherein the flow tube holder defines a cavity and the flow tube is positioned within the flow tube holder cavity such that a press-fit engagement is formed between the flow tube holder and the flow tube.

16. The conductivity cell of claim 14, wherein the inner diameter of the flow tube holder is configured to control the axial and radial positions of the electrodes in the flow tube.

17. The conductivity cell of claim 14 wherein the end cap is positioned in the open second end of the flow tube holder such that a press-fit engagement is formed between the end cap and the second end of the flow tube holder.

18. The conductivity cell of claim 14 wherein the flow through hole is a smooth surface.

19. The conductivity cell of claim 14 wherein the first end fitting and the second end fitting are configured to connect to a fluid line.

20. A conductivity cell comprising:
a cylindrical flow tube holder having a closed first end and an open second end;
a first end fitting positioned on the first end of the flow tube holder;
a second end fitting positioned on the second end of the flow tube holder;
a flow tube positioned within the flow tube holder;
an end cap positioned in the open second end of the flow tube holder and adjacent the flow tube and the second end fitting;
a plurality of electrodes positioned in the flow tube;
a plurality of o-rings positioned on the electrodes; and
a flow through hole extending from the first end fitting through the flow tube holder, the flow tube, and the end cap to the second end fitting;
wherein the flow tube holder defines a cavity and the flow tube is positioned within the flow tube holder cavity such that a press-fit engagement is formed between the flow tube holder and the flow tube; and
wherein outer ends of the electrodes are in contact with an inner wall of the flow tube holder and inner ends of the electrodes form part of the flow through hole.

21. A conductivity cell comprising:
a cylindrical flow tube holder having a closed first end and an open second end;
a first end fitting positioned on the first end of the flow tube holder;
a second end fitting positioned on the second end of the flow tube holder;
a flow tube positioned within the flow tube holder;
an end cap positioned in the open second end of the flow tube holder and adjacent the flow tube and the second end fitting;
a plurality of electrodes positioned in the flow tube, wherein each electrode of the plurality of electrodes includes a cylindrical stem extending from an inner end of a main body of the electrode to the flow through hole and a groove on the inner end of the main body of the electrode, wherein the groove surrounds the stem;
a plurality of o-rings positioned on the electrodes, wherein the groove is configured to receive an o-ring of the plurality of o-rings; and
a flow through hole extending from the first end fitting through the flow tube holder, the flow tube, and the end cap to the second end fitting.

* * * * *

UNITED STATES PATENT AND TRADEMARK OFFICE
CERTIFICATE OF CORRECTION

| | |
|---|---|
| PATENT NO. | : 10,571,419 B2 |
| APPLICATION NO. | : 15/604231 |
| DATED | : February 25, 2020 |
| INVENTOR(S) | : Thomas Lenagh, Rudy Pitera and Tomas Lorincz |

Page 1 of 1

It is certified that error appears in the above-identified patent and that said Letters Patent is hereby corrected as shown below:

In the Claims

Column 15, Line 24 Claim 14:
Delete "flaw"
Insert --flow--

Signed and Sealed this
Thirtieth Day of June, 2020

Andrei Iancu
*Director of the United States Patent and Trademark Office*